United States Patent [19]

Bujard

[11] Patent Number: 4,862,384
[45] Date of Patent: Aug. 29, 1989

[54] METHOD OF MEASURING THE DYNAMIC VISCOSITY OF A VISCOUS FLUID UTILIZING ACOUSTIC TRANSDUCER

[75] Inventor: Martial R. Bujard, Hinterkappelen, Switzerland

[73] Assignee: Rockwell International Corporation, El Segundo, Calif.

[21] Appl. No.: 81,042

[22] Filed: Aug. 3, 1987

[51] Int. Cl.[4] ..................... G01N 11/00; G01N 29/02
[52] U.S. Cl. ........................................ 364/509; 73/54; 73/599; 364/556
[58] Field of Search ..................... 364/556, 507-510; 73/590, 599, 54

[56] References Cited

U.S. PATENT DOCUMENTS

| H465 | 5/1988 | Brown ................................. 73/590 |
| 2,707,391 | 5/1955 | McSkimin . |
| 2,735,662 | 7/1956 | Swengel ............................... 73/54 |
| 3,194,057 | 7/1965 | Richard . |
| 3,382,706 | 5/1968 | Fitzgerald et al. . |
| 3,435,664 | 4/1969 | Harris . |
| 3,553,636 | 1/1971 | Baird . |
| 3,751,974 | 8/1973 | Urbas . |
| 4,193,291 | 3/1980 | Lynnworth ...................... 73/32 A |
| 4,312,228 | 1/1982 | Wohltjen ........................... 73/597 |
| 4,341,111 | 7/1982 | Husar ................................ 73/64.1 |
| 4,441,358 | 4/1984 | Osborne .............................. 73/55 |
| 4,505,154 | 3/1985 | Wiesner ........................... 73/150 R |
| 4,558,588 | 12/1985 | Beaudoin et al. ................... 73/54 |
| 4,559,810 | 12/1985 | Hinrichs et al. .................... 73/54 |
| 4,602,505 | 7/1986 | Kanda et al. ........................ 73/54 |
| 4,612,800 | 9/1986 | Erian .................................. 73/54 |
| 4,630,465 | 12/1986 | Hatton ............................... 73/35 |
| 4,662,222 | 5/1987 | Johnson ............................ 73/602 |
| 4,721,874 | 1/1988 | Emmers ............................. 73/54 |

FOREIGN PATENT DOCUMENTS

| 0913165 | 3/1982 | U.S.S.R. ............................... 73/54 |
| 0926590 | 5/1982 | U.S.S.R. ............................... 73/54 |
| 0958911 | 9/1982 | U.S.S.R. ............................... 73/54 |

OTHER PUBLICATIONS

Donald L. Hunston, "Determination of the High Frequency Viscoelastic Properties of Polymers Using Shear Mode Strip Delay Lines", 12/1971, J. Polymer Sci: Part C, No. 35, pp. 201-210.

Lea et al., The Transverse Acoustic Impedance of an Inhomogeneous Viscous Fluid, Ultrasonics, Vol. 23 (May 1985).

Harrison et al., Dynamic Viscosity Measurement in Methods of Experimental Physics: Ultrasonics, vol. 19, Chapter 3, pp. 137-178 (Academic Press 1981).

Primary Examiner—Parshotam Lall
Assistant Examiner—S. A. Melnick
Attorney, Agent, or Firm—H. Frederick Hamann; Craig O. Malin; John J. Deinken

[57] ABSTRACT

The dynamic viscosity of a viscous medium is measured by positioning an acoustic transducer in the temperature and pressure environment of the medium and spaced from the medium, then measuring a first resonant frequency and bandwidth for acoustic shear wave propagation within the transducer. The transducer is then positioned in surface contact with the medium, and a second resonant frequency and bandwidth are measured. The viscosity of the medium is calculated from the difference between the first and second resonant frequencies and bandwidths. The step of measuring a first resonant frequency and bandwidth involves applying a first input signal to the transducer to generate acoustic shear waves within the transducer, measuring the frequency and amplitude of the output signal produced by the transducer in response to the acoustic shear waves, and repeating the steps of applying and measuring for a range of first input signal frequencies to determine a first resonant frequency and bandwidth for the transducer. Similarly, the step of measuring a second resonant frequency and bandwidth includes applying a second input signal to the transducer to generate acoustic shear waves within the transducer, measuring the frequency and amplitude of the output signal produced by the transducer in response to the acoustic shear waves, and repeating the steps of applying and measuring for a range of second input signal frequencies to determine a second resonant frequency and bandwidth for the transducer.

5 Claims, 4 Drawing Sheets

METHOD OF MEASURING THE DYNAMIC VISCOSITY OF A VISCOUS FLUID UTILIZING ACOUSTIC TRANSDUCER

BACKGROUND OF THE INVENTION

This invention is concerned with acoustic techniques for measuring the dynamic viscosity of a material, and particularly with the measurement of the viscosity of a composite material during the curing process for the composite.

A composite material typically includes a base or substrate material, such as a thermally cured polymer ior epoxy resin, the substrate being strengthened by the addition of a fibrous component such as carbon, graphite, boron, or nylon. Composites exhibit extremely high strength-to-weight ratios in comparison to other structural materials. As a result, their use is becoming increasingly important in applications which require high strength as well as light weight, such as the manufacture of aerospace vehicles.

In fabricating a structure with composite materials, a part is manufactured by first positioning layers of raw or partially cured composite materials in a mold. When the desired shape has been built up, the part is subjected toi a curing process in a pressurized oven known as an autoclave. Under the influence of an elevated temperature in the autoclave, the polymer molecules of the resin grow into longer chains and branches, and cross links between the chains are formed. In this manner, the polymerization of the resin substrate is completed, causing the molded shape to become permanent and leaving the composite material hard and durable.

The composite production process may be usefully characterized by continuously measuring the structural parameters of the composite during the solidification of the material. One important parameter of the curing material which is influenced by the rate of the curing reaction is the viscosity of the resin substrate. Knowledge of the changing viscosity can be used, for example, to minimize porosity in the final product. Measuring the process, however, presents some difficult problems. The rate at which the curing reaction proceeds is a complex function of temperature and pressure which depends, inter alia, upon the thickness and geometry of the part being fabricated, the thermal equilibrium between the part and the mold, the temperature of the environment around the part, and the thermal mass of the autoclave. At times during the cure, the viscosity will be low enough to allow the resin to flow. Although a controlled flow of the resin may be desirable to achieve the required thickness or strength in the part, if the resin is allowed to flow upredictably, microvoids or variations in the thickness of the part can result. Consequently, control of the resin viscosity is an important aspect of the cure process.

For any given part geometry, the flow of the resin is determined by its viscosity and ambient pressure. The viscosity of the resin is, in turn, a function of temperature and of the time the resin has been subjected to the final curing process. Thus, the temperature and pressure can be varied during the cure cycle to control changes in the viscosity. For a particular resin and a given variation in temperature during the cure cycle, it is theoretically possible to predict the viscosity of the resin at any time during the cure cycle. Consequently, process control technicues in the prior art have involved monitoring the temperature and pressure during the cure cycle and adjusting these parameters, either manually or by computer control, in an attempt to maintain the viscosity of the composite at the theoretical ideal.

It has been found, however, that actual variations in the viscosity of the resin during the cure cycle frequently do not match the predicted viscosity profile. This is due to a number of factors, such as variations in the moisture content of the resin or disparities in the production techniques used to make the pre-impregnated resin. Furthermore, the polymerization and crosslinking reactions of the resin, which ideally occur only during the final cure step, also proceed, albeit at a slower rate, in the pre-impregnated resin. Thus, even resins having the same original chemical composition may exhibit different states of polymerization when the final curing process is initiated and will therefore display somewhat different viscosity profiles under the same cure conditions. Consequently, it is desirable to monitor temperature, pressure, and, most important, viscosity at various locations on the part and at various times during the cure cycle, and to adjust the applied temperature and pressure in accordance with the disparity between the desired temperature, pressure, and viscosity profiles and the measured values.

Although mechanical measurements of viscosity have been made in the prior art, a mechanical approach requires the insertion of a probe into the measured component. This is generally not feasible during the manufacture of a composite part, especially when the viscosity must be measured at different times during the cure cycle and at numerous locations within the composite part. Chemical techniques, such as high performance liquid chromatography, differential scanning calorimetry, and infrared spectroscopy, are also known in the art for monitoring the cure state of a resin. These techniques, however, are difficult to implement in a manufacturing environment. Another method which has been used to measure the viscosity is to relate it to changes in the substrate's dielectric properties. This method, however, suffers from a lack of reliability and low signal-to-noise ratios.

A variety of acoustic testing methods have alsio been employed to measure resin viscosity. A class viscometer, such as the torsional torque viscometer, mechanically measures the force required to turn a vane or propeller-like structure inserted into the test liquid. Using ultrasound to measure viscosity implies that the viscosity is measured at high frequencies. The viscosity so measured, which is known as the dynamic viscosity, is much lower in value than the viscosity usually measured with a classical viscometer, because the high frequencies involved require more rapid motions in the viscous medium than are associated with relaxations in the medium. Nevertheless, the behavior of viscosity as a function of temperature or pressure has been observed to be similar at high and low frequencies. Consequently, the dynamic viscosity is a useful parameter for describing the state of the viscous medium. In addition, a potential advantage of using the propagation of ultrasonic waves to measure the viscosity of a medium is that the wave propagation depends directly on the mechanical constants of the medium of propagation. Ultrasonic data analysis techniques provide algorithms for deriving these mechanical constants from the measured propagation characteristics. The usual acoustic technique of measuring the attenuation of longitudinal waves propagating in the viscous medium requires many assumptions and many conditions to be fulfilled that limit its applicability. All the other causes of ultrasonic attenuation, for example, such as diffraction, dispersion, and thermoelastic loss, must be negligible in comparison to the viscous loss. In addition, the sum of the volume and shear viscosities is measured, rather than only the shear viscosity. Furthermore, in longitudinal wave techniques the ratio of the imaginary part of the bulk modulus to the real part must usually be assumed to be much lower than unity. The viscous medium must have sufficient thickness that the different echoes in the pulse-echo train can be resolved, yet be thin enough that the first echoes are detectable, and internal reflections inside the composite laminates must be assumed to be negligible. Other ultrasonic methods known in the prior art for measuring viscosity use the reflection of plane shear waves, resonance techniques, or guided travelling waves.

One method used to measure the dynamic viscosity of a medium is to first launch a pulse in a solid (a buffer rod) which is not in contact with the viscous medium. This measurement provides a reference waveform for the vibration characteristics of the buffer rod alone. Another pulse is generated after the buffer rod is placed in contact with the viscous medium. The received waveform is then compared with the reference waveform. From the results of these twio measurements, the viscosity can readily be deduced. By decinvolution, the reference signal allows unwanted information, such as transducer frequency characteristics, changes of velocity and attenuation of the buffer material with temperature, and changes of buffer length with temperature, to be removed. A double buffer with a partially reflecting interface has also been used to provide the reference. In the latter arrangement, the time domain is used to separate the reference signal from the unknown resin signal. This requires the use of short pulses which can be time-resolved sufficiently to give them separate treatments in signal processing.

This method for measuring the dynamic viscosity suffers from two disadvantages, both related to the fact that the change of phase due to the presence of the viscous medium is extremely small. The bond between the piezoelectric element and the buffer rod must be the same for both measurements, and the length of the buffer rod must not change. When variations in temperature or pressure occur, these two conditions may be hard to fulfill.

Thus the acoustic methods known in the prior art are limited in their ability to monitor viscosity at high temperatures, cannot measure high values of viscosity, and suffer from inaccuracies introduced by such factors as temperature instability, stray capacitance, and unreliable bonds between portions of the acoustic apparatus. In particular, the acoustic techniques known in the prior art require either partial or total immersion of the testing apparatus in the liquid whose viscosity is to be measured. This requirement is unacceptable in such applications as the composite curing environment, where the structural integrity of the curing part could thereby be adversely affected.

SUMMARY OF THE INVENTION

This invention uses the resonance of ultrasonic shear waves propagating within a transducer in contact with a viscous medium to measure the viscosity of the medium with high precision in extreme environments without breaching the structural integrity of the medium being measured.

The dynamic viscosity of a viscous fluid is measured by positioning an acoustic transducer in the temperature and pressure environment of the fluid and spaced from the fluid, then applying a first input signal to the transducer to generate acoustic shear waves within the transducer. The frequency and amplitude of the output signal produced by the transducer in response to the acoustic shear waves are measured. These steps are repeated for a range of input signal frequencies to determine a first resonant frequency and bandwidth for acoustic shear wave propagation within the transducer. The transducer is then positioned in the temperature and pressure environment of the fluid and in surface contact with the fluid, and a second input signal is applied to the transducer to generate acoustic shear waves within the transducer. The frequency and amplitude of the output signal produced by the transducer while in contact with the viscous medium are measured. These steps are repeated fior a range of input signal frequencies while the transducer is in contact with the viscous medium to determine a second resonant frequency and bandwidth for acoustic shear wave propagation within the transducer. Finally, the viscosity of the fluid is calculated using the shift between the first and second resonant frequencies and the difference between the first and second bandwidths.

In a more particular embodiment, the step of measuring a first resonant frequency and bandwidth involves applying a first input signal to the transducer to generate acoustic shear waves within the transducer, measuring the frequency and amplitude of the output signal produced by the transducer in response to the acoustic shear waves, and repeating the steps of applying and measuring for a range of first input signal frequencies to determine a first resonant frequency and bandwidth for the transducer. Similarly, the step of measuring a second resonant frequency and bandwidth includes applying a second input signal to the transducer to generate acoustic shear waves within the transducer, measuring the frequency and amplitude of the output signal produced by the transducer in response to the acoustic shear waves, and repeating the steps of applying and measuring for a range of second input signal frequencies to determine a second resonant frequency and bandwidth for the transducer.

The step of calculating the viscosity of the fluid may be accomplished by first calculating the order m of the first and second resonant frequencies from the expression $$m = \frac{a \, \omega_{0m}}{2\pi v}$$

where a is twice the thickness of the transducer, $\omega_{0m}$ is the first resonant frequency, and v is the velocity of acoustic shear wave propagation within the transducer. The phase $\delta$ of the reflection coefficient is then calculated from the expression $$\delta = -\pi - m2\pi\Delta\omega_m/\omega_{0m}$$

where $\Delta\omega_m$ is the shift in the mth resonance. The amplitude $r_o$ of the reflection coefficient is calculated from the expression $$r_o = \exp(\alpha a) \frac{1 + \sin((\omega_{1m}/\omega_{0m})m2\pi - \delta - \pi)}{\cos((\omega_{1m}/\omega_{0m})m2\pi - \delta - \pi)}$$

where $\alpha$ is the attenuation in the transducer and $\omega_{1m}$ is the frequency at which the transducer particle displacement in quadrature with the input signal is at a maximum. Finally, the dynamic viscosity $\eta$ is obtained by substituting the calculated values for $r_o$ and $\delta$ into the expression:

$$\eta = \frac{Z_1^2}{\rho\omega} \frac{(1-r_0^2)4r_0 \sin\delta}{[(1-r_0\cos\delta)^2 + (r_0\sin\delta)^2]^2}$$

where $Z_1$ is the acoustical impedance of the viscous medium, $\omega$ is the second resonant frequency, and $\rho$ is the density of the viscous medium.

In the case where the transducer is a piezoelectric transducer, the step of applying a first input signal to the transducer is accomplished by applying a first alternating current input electrical signal to the transducer to generate acoustic shear waves within the transducer and the step of applying a second input signal to the transducer involves applying a second alternating current input electrical signal to the transducer to generate acoustic shear waves within the transducer. The steps of measuring the frequency and amplitude f the output signal from the transducer involve measuring the frequency and amplitude of the output electrical signal produced by the transducer in response to the acoustic shear waves.

DESCRIPTION OF THE INVENTION

Figure 1:
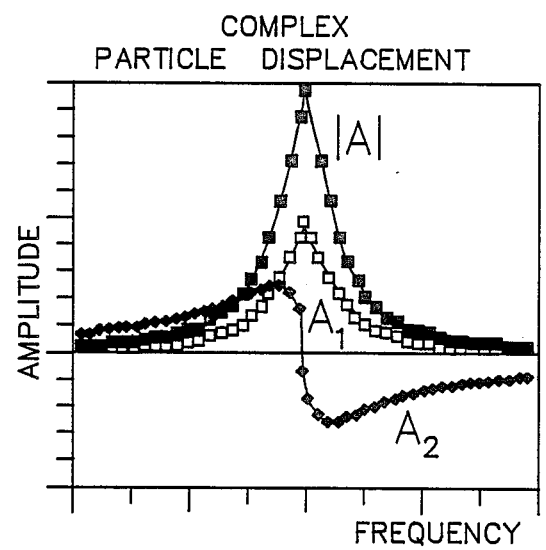
FIG. 1 is a plot of the real and imaginary parts and the amplitude of the complex particle displacement as a function of frequency depicting one of the frequencies at which a mechanical resonance of an acoustic transducer occurs.

In this invention, the dynamic viscosity of a viscous medium is deduced by measured the resonance characteristics of an acoustic transducer in contact with the viscous medium. In an outstanding feature of this invention, however, the buffer rod used as the solid in such a measurement in the prior art is eliminated. Instead, the transducer itself ie employed as the solid and is placed in direct contact with the viscous medium to establish the viscous medium-solid interface. Since there is no buffer rod, this approach avoids the problems caused by changes in the bond between the piezoelectric element and the buffer rod and eliminates as well the inaccuracies which could be introduced due to changes in the length iof the buffer rod.

The viscosity measurement technique of this invention requires an expression for the relationship between the complex reflection coefficient and the complex shear modulus of a viscous medium. The shear modulus G of a viscous medium may be written as a complex number:

$$G = G' + iG'' \tag{1}$$

where $G'$ is the elastic modulus and $G''$ is related to the dynamic viscosity $\eta$, at a given frequency $\omega$, by:

$$G'' = \eta\omega \tag{2}$$

The expression of Equation (2) assumes that the viscous forces are proportional to the velocity of particle displacements in the viscous medium.

Both $G'$ and $G''$ can be obtained by generating a shear wave in the transducer and measuring the reflection of the shear wave at the interface between the transducer nd a viscous medium. The reflection coefficient r at the interface is a function of the acoustical impedances $Z_1$ and $Z_2$ of the viscous medium and the transducer, respectively:

$$r = (Z_2 - Z_1)/(Z_2 + Z_1) \tag{3}$$

where $$Z_2 = \sqrt{(G' + iG'')\rho} \tag{4}$$

$$Z_1 = \sqrt{G_s \rho_s}$$

$\rho$ being the density of the viscous medium, $G_s$ the shear modulus of the solid, and $\rho_s$ the density of the solid. $G_s$, $\rho_s$, and $Z_1$ can be obtained from other measurements or as known values from a table.

The impedance $Z_2$ is a complex number, as thus is r, which can be written as:

$$r = r_o \exp(i\delta) \tag{5}$$

where $r_o$ is the amplitude and $\delta$ the phase of the reflectioncoefficient. Inserting Equations (4) and (5) into Equation (3) and solving for $G'$ and $G''$ yields:

$$G' = \frac{Z_1^2}{\rho} \frac{(1-r_0^2)^2 - (2r_0\sin\delta)^2}{[(1-r_0\cos\delta)^2 + (r_0\sin\delta)^2]^2} \tag{6a}$$

$$G'' = \eta\omega = \frac{Z_1^2}{\rho} \frac{(1-r_0^2)4r_0 \sin}{[(1-r_0\cos\delta)^2 + (r_0\sin\delta)^2]^2} \tag{6b}$$

Considering now the vibration of an ultrasonic transducer in contact with a viscous medium, it is assumed that the faces of the transducer are parallel and that the acoustic wave propagates within the transducer in a direction normal to its faces. It is also assumed that no mode conversion occurs upon reflection of the wave at the interface.

For continuous wave excitation under these conditions, the complex particle displacement A(t) for the surface of the transducer is given by:

$$A(t) = A_0 \exp(i\omega t)[1 + \quad (7)$$
$$r_0 \exp\{-(\alpha a + i(ka - \delta - \pi))\} +$$
$$r_0^2 \exp\{-2(\alpha a + i(ka - \delta - \pi))\} + \ldots]$$

where
- $A_o$ is the initial displacement
- $\omega$ is the frequency of the driving voltage
- t is the time dependence of the shear wave
- $\alpha$ is the attenuation in the transducer
- a is twice the thickness of the transducer
- k is the wave number in the transducer
- $r_o \exp(i\delta)$ is the reflection coefficient at the viscous medium-solid interface The successive terms in the bracketed portion of Equation (7) represent the contributions to the particle displacement after 0, 1, 2, ... round trips of acoustic energy in the transducer. These terms form a geometric series, which can be summed so that the expression for A(t) becomes:

$$A(t) = A_o \exp(i\omega t)[1/(1 - r_o \exp\{-(\alpha a + i(ka - \delta - \pi))\})] \quad (8)$$

$A_1$ and $A_2$ are respectively defined as the particle displacement in phase and in quadrature with the driving voltage:

$$Re\{A(t)\} = A_1 \cos(\omega t) - A_2 \sin(\omega t) \quad (9)$$

so that:

$$A_1 = \quad (10a)$$
$$A_0 \frac{1 - r_0 \exp(-\alpha a) \cos(ka - \delta - \pi)}{1 - 2 r_0 \exp(-\alpha a) \cos(ka - \delta - \pi) + r_0^2 \exp(-2\alpha a)}$$

and $$A_2 = \quad (10b)$$
$$-A_0 \frac{r_0 \exp(-\alpha a) \sin(ka - \delta - \pi)}{1 - 2 r_0 \exp(-\alpha a) \cos(ka - \delta - \pi) + r_0^2 \exp(-2\alpha a)}$$

Figure 2:
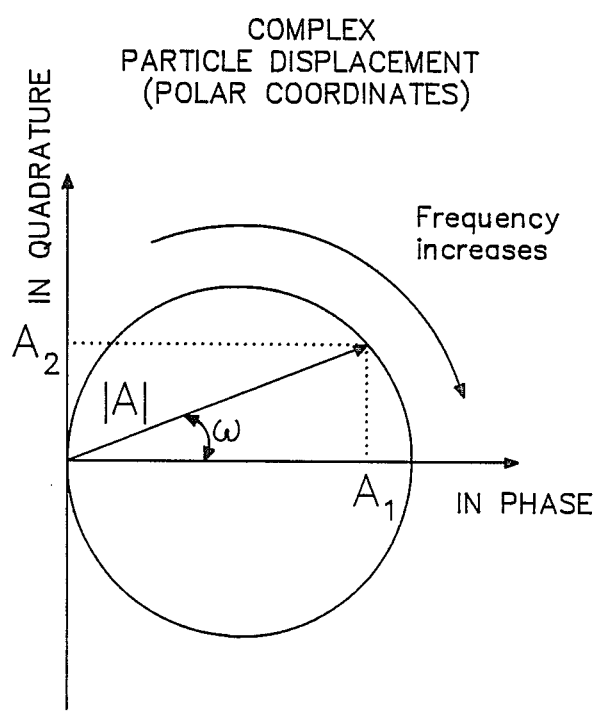
FIG. 2 is a plot illustrating the resonance depicted in FIG. 1, but using a polar coordinate representation.

A plot of Equations (10a) and (10b) as a function of frequency will display a set of equally spaced frequencies at which a mechanical resonance of the transducer occurs. FIG. 1, which is a plot of $A_1$, $A_2$, and $|A|^2$ as functions of frequency (the vertical scale for $|A|^2$ is expanded with respect to that for $A_1$ and $A_2$), depicts one of these resonances, while FIG. 2 illustrates this same resonance using a polar coordinate representation. The condition for the mth resonance is that the total particule displacement must be in phase with the driving voltage ($A_2=0$ and $A_1$ is at a maximum), i.e.:

$$ka - \delta - \pi = m2\pi \quad m = 1, 2, 3 \ldots \quad (11)$$

$$\omega_m = \frac{(m2\pi + \delta + \pi)v}{a} \quad m = 1, 2, 3 \ldots \quad (12)$$

where v is the velocity of the elastic wave in the transducer ($\omega = kv$). The separation of the resonances will generally be sufficient to allow a good estimate to be made for the order m of the measured resonance from knowledge of the transducer thickness and control of the frequency imposed on the system.

For a freely vibrating transducer which is not in contact with a viscous fluid, $r_o = 1$ and $\delta = -\pi$, so that the free resonance vibrations $\omega_{om}$ are given by:

$$\omega_{0m} = \frac{m2\pi v}{a} \quad m = 1, 3, 5 \ldots \quad (13)$$

The boundary conditions imply that only odd values of m are allowed.

The complex reflection coefficient r for vibrations when the transducer is contacting the medium can be deduced from the preceding relations. From the shift $\Delta\omega_m = \omega_{om} - \omega_m$ of the mth resonance, the phase $\delta$ of the reflection coefficient (Equations (12) and (13)) can easily be computed:

$$\delta = -\pi - m2\pi\Delta\omega_m/\omega_{om} \quad (14)$$

The amplitude $r_o$ of the reflection coefficient can be deduced from $\omega_{1m}$ and $\omega_{2m}$, which correspond to the maximum and minimum of $A_2$ ($\partial A_2/\partial\omega=0$) around the mth resonance. Using Equation (13) with $\omega_{1m}$:

$$r_0 = \exp(\alpha a) \frac{1 + \sin((\omega_{1m}/\omega_{0m})m2\pi - \delta - \pi)}{\cos((\omega_{1m}/\omega_{0m})m2\pi - \delta - \pi)} \quad (15a)$$

and with $\omega_{2m}$ $$r_0 = \exp(\alpha a) \frac{1 - \sin((\omega_{2m}/\omega_{0m})m2\pi - \delta - \pi)}{\cos((\omega_{2m}/\omega_{0m})m2\pi - \delta - \pi)} \quad (15b)$$

The viscosity of the medium can then be obtained by inserting the values thus calculated for $r_o$ and $\delta$ into Equation (6b) and solving the equation for the viscosity $\eta$. G' can also be calculated from Equation (6a), but is not required for the viscosity measurement.

Figure 3:
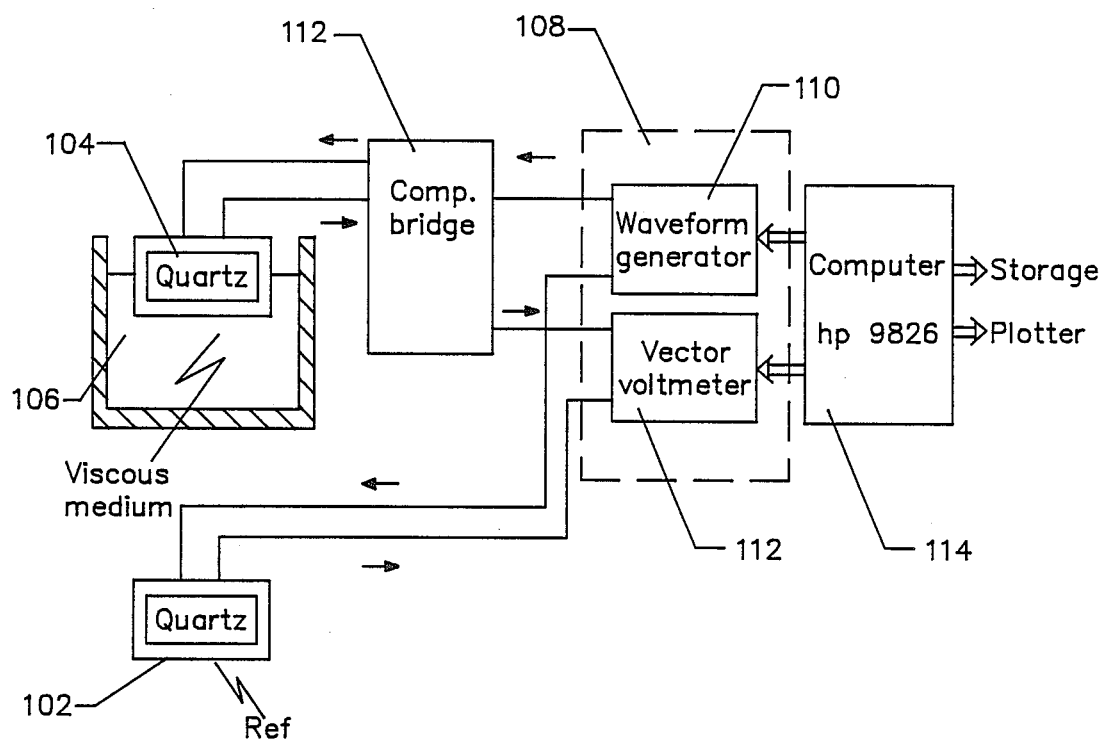
FIG. 3 is a schematic block diagram of one apparatus which has been used to perform the viscosity measurement technique of this invention.

FIG. 3 is a schematic block diagram of one apparatus which has been used to perform the measurement technique of this invention. A first piezoelectric transducer 102 is used as a reference transducer, while a second piezoelectric transducer 104 is placed in surface contact with the viscous medium 106 which is to be measured. The reference piezoelectric element provides two items of information: the free resonance frequency $\omega_{om}$ and the attenuation $\alpha$ if the piezoelectric element at the pressure and temperature present in the oven.

A network analyzer 108 container a waveform generator 110 and a vector voltmeter 112 is used for the excitation and detection of the vibrations of the transducers. The waveform generator, used in its continuous wave mode, is programmed to scan the frequencies around a known resonant frequency of the reference transducer 102. The vector voltmeter measures the amplitude and the phase of the signal S coming from the transducer. These measurements allow a polar plot of the resonance to be drawn, as shown in FIG. 2, instead of the plot of the amplitude of S as a function of frequency, as shown in FIG. 1. A compensation bridge 112 is used to compensate for the static capacitance of the reference transducer 104. A computer 114 controls the entire operation and treats the data in real time.

Figure 4:
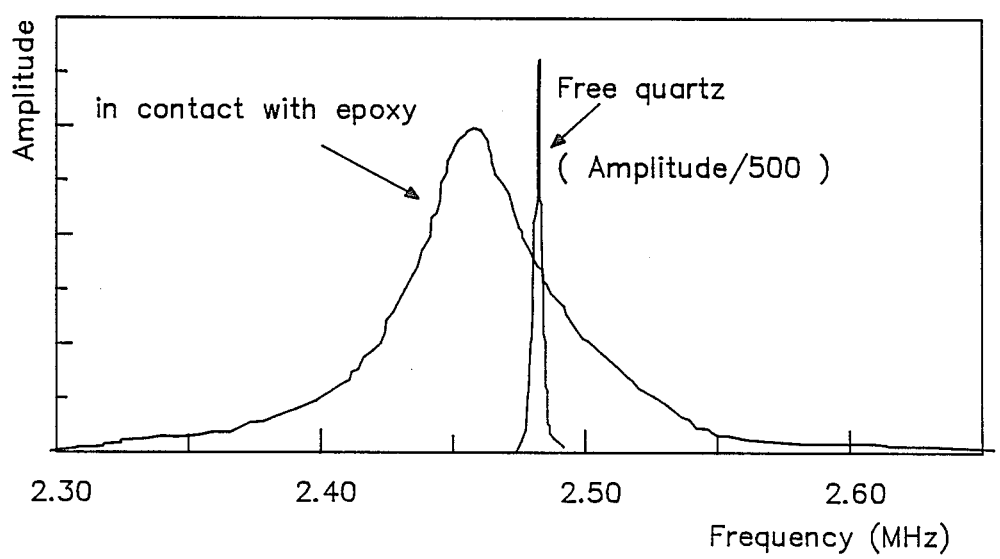
FIG. 4 depicts the response of a piezoelectric element under idealized conditions of free vibration and when in contact with a layer of epoxy.

The continuous wave excitation of the transducer 104 causes a resonance to be set up within the transducer. When the transducer is placed in contact with the viscous medium, measurements are made of the change in the peak frequency of this resonance, $\Delta f$, and of the change in its width, $\Delta Q^{-1}$. From $\Delta f$ and $\Delta Q^{-1}$, $r_o$ and $\delta$ can be readily computed, then the viscosity and elasticity of the medium can be deduced from Equation 6. The change in the width of the resonance $\Delta Q^{-1} = \Delta\omega/\omega$ yields the attenuation $\alpha$ and therefore the amplitude of the reflection coefficient $r_o$ from Equation (15). The phase shift $\delta$ depends on the shift in the resonant frequency $\Delta f$. The response of a piezoelectric element under conditions of free vibration and when in contact with epoxy is shown in FIG. 4. The shift of the resonant frequency and the increase in the bandwidth is evident. The amplitude of vibration of the free quartz element is much greater (approximately 500 times) than that of the quartz element in contact with epoxy. Also, the shift in resonant frequency is large—30 kHz in this example.

Figure 5:
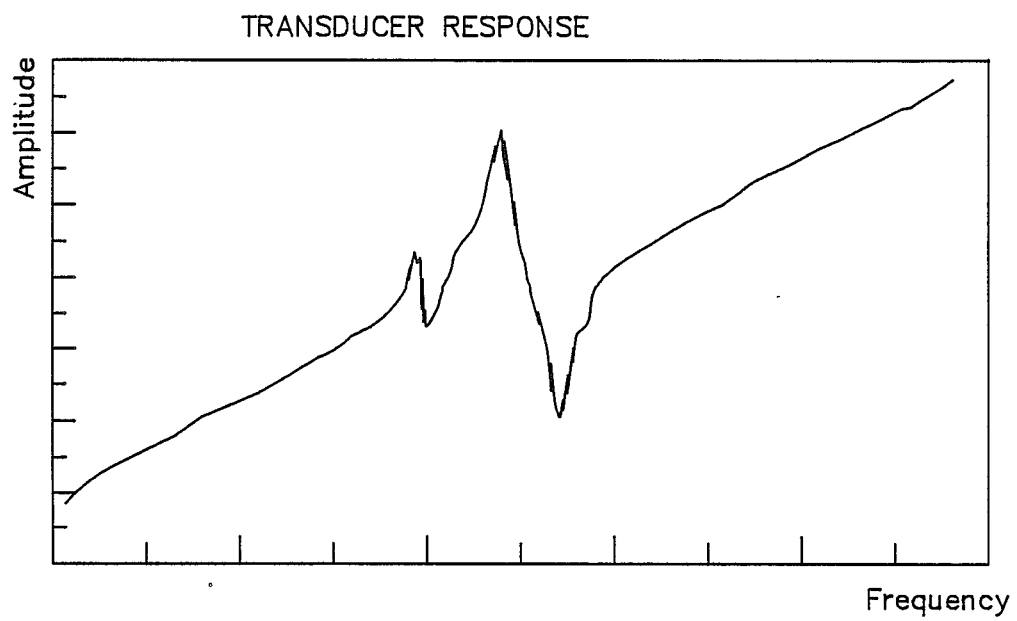
FIG. 5 is a more realistic plot of the amplitude response of a piezoelectric transducer signal as a function of frequency, including a spurious resonance, an ill-defined peak, and a general increase of the signal amplitude with frequency.

The data for FIG. (4) was obtained under idealized conditions, with short cables, careful temperature control, and a thin film of epoxy carefully placed on the transducer. A realistic plot of the amplitude of S as a function of frequency is shown in FIG. 5, which displays data obtained with more realistic conditions, i.e., longer signal cables and the transducer placed on an actual composite part in an oven. A spurious resonance, an ill-defined peak, and a general increase of the signal amplitude with frequency can be seen.

The absence of a well-defined peak and the general increase in signal amplitude are both consequences of the parasitic capacitances of the cables, the piezoelectric element holder, and also of any uncompensated static capacitance of the piezoelectric element itself. The effect of the poorly defined peak and the increase in signal amplitude on the accuracy of the signal analysis can be minimized using the polar representation shown in FIG. 6.

Figure 6:
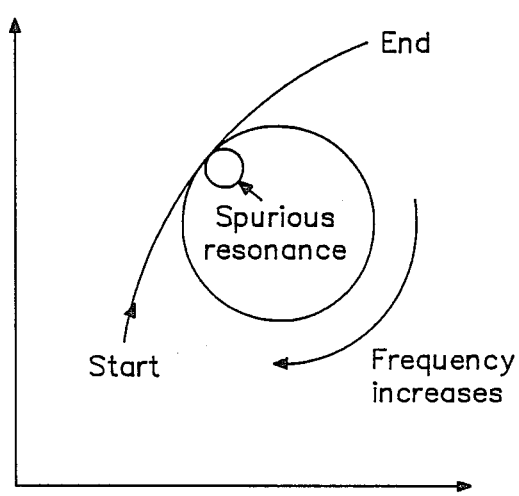
FIG. 6 is a plot of the data shown in FIG. 5, but using a polar coordinate representation.
Figure 7:
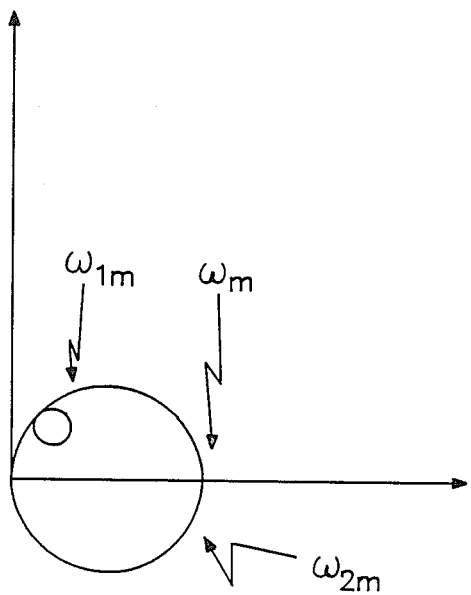
FIG. 7 is a plot of the data shown in FIG. 6 with the data translated to the coordinate orgin.

In FIG. 6, the spurious resinance appears as a small circle within the large circle corresponding to the resonance of interest. Moreover, the circle is translated away from the origin. FIG. 7 shows the same data after translating the circle back to the origin. The frequencies corresponding to the north pole, the south pole, and the east point of the greatest circle are then easily determined. They are, respectively, $\omega_{1m}$, $\omega_{2m}$, and $\omega_m$. The resonant frequency, $\omega_m$, is usually different from the frequency at which the signal S reaches its maximum (FIG. 5).

For highly viscous media, the signal to noise ratio diminishes and the north pole, south pole, and east point may be difficult to locate. Two methods have been developed to handle this case. By digital filtering of the data, the circle can be smoothed, or a fit of the data by the analytical expressions for $A_1$ and $A_2$ can be accomplished. Using the first method, the results of the dynamic viscosity measurements have a dispersion of 10%; using the second one, the dispersion is reduced to 1%.

EXAMPLE 1

Viscosity measurements of a graphite-epoxy composite were made during the cure stage. For these measurements the piezoelectric element (quartz) was not put directly in contact with the composite, but a release foil was interposed between the transducer and the composite. The foil allowed the quartz element to be removed from the graphite-epoxy plate after the end of the cure and reused for other measurements.

The temperature profile of the cure cycle included four phases:

1. T = 107° C. for 30 minutes.
2. T increased from 107° to 175° C.
3. T = 175° C. for 75 minutes.
4. T decreased to room temperature.

Figure 8:
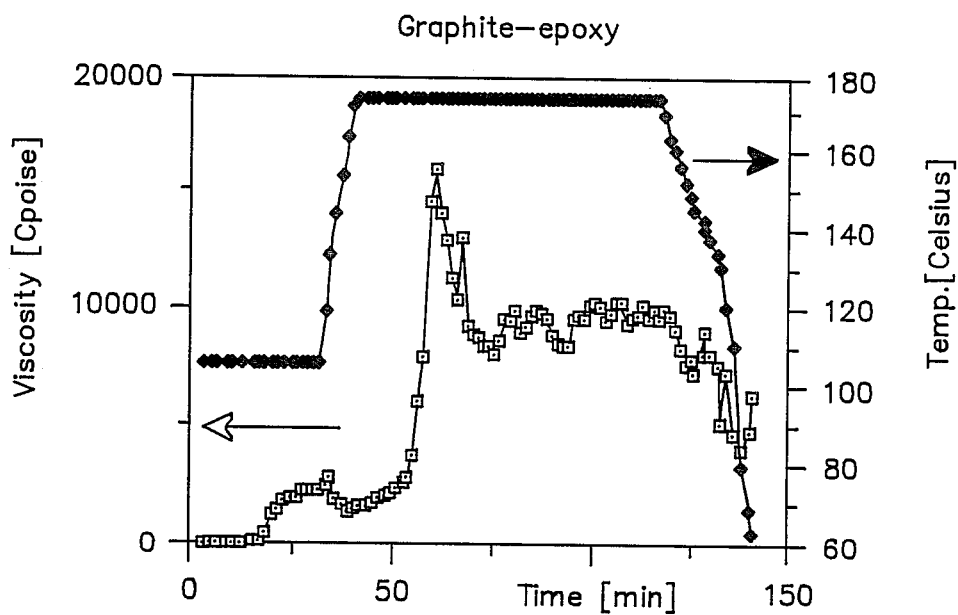
FIG. 8 is a plot of measured viscosity as a function of time for the cure cycle of a composite part.

As shown in FIG. 8, at the beginning of the cure cycle, the measured viscosity was zero because no epoxy was touching the quartz element. As some of the epoxy flowed through the release foil, it made contact with the quartz element and the measured viscosity begin to increase. When the temperature was increased in the second portion of the cure cycle, the viscosity decreased as expected. During the third portion of the cycle, the viscosity first reached a peak and then decreased to a constant value of approximately 100 poise. This behavior is probably because most of the chemical reaction activity in the graphite-epoxy composite takes place just after reaching 175° C., giving rise to the peak of viscosity. When the viscosity went down to 100 poise, the cure itself had ended. During the fourth part of the cure cycle, the measured dynamic viscosity decreased, but this feature may be due to a shrinkage effect, which can alter the resonance of the quartz element.

The technique of this invention for making viscosity measurements provides accurate and easily obtained values. It may be readily implemented in a factory or productiion environment. The inventive method is capable of operation at temperatures from room temperature to 200° C., and can potentially extend up to 400° C. In addition, viscosity measurements can be made at different frequencies with a single apparatus. Its main advantages compared to conventional techniques involving reflection of shear waves or resonance techniques are:

1. No buffer rod is required, making the measurements more convenient, while the problem of invariance in the bond between the piezoelectric element and the buffer rod, which is required by the standard reflection technique, is avoided.
2. No temperature stabilization is required. With the standard reflection technique, temperature stabilization to better than 0.003° C. is necessary.
3. The polar representation of data allows the elimination of stray capacitances that are difficult to compensate for using a bridge network or reference arm.
4. Values of viscosity as high as 600 poise can be measured, whereas the usual resonance techniques restrict the maximum measurable value to 10 poise.

The preferred embodiments of this invention have been illustrated and described above. As with all reflection techniques, this technique measures the near surface dynamic viscosity which may, in some cases, be different from the shear viscosity of the bulk medium. Many spurious resonances may be observed with siome piezoelectric elements. They can be partially removed by using special plating. Alternatively, if a spurious resonance exists at or near the resonance of interest, the piezoelectric element may be changed. When two transducers are used, the two must be matched, i.e., they must exhibit the same resonant frequencies when freely vibrating without contact with a viscous medium. Since it is sometimes difficult to obtain two transducers which are matched, it may be necessary to incorporate a correction factor in the calculations. Other modifications and additional embodiments will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method of measuring the dynamic viscosity of a viscous fluid, comprising the steps of:

positioning an acoustic transducer in the temperature and pressure environment of the fluid and spaced from the fluid;

applying a first input signal to the transducer to generate acoustic shear waves within the transducer;

measuring the frequency and amplitude of the output signal produced by the transducer in response to the acoustic shear waves;

repeating the steps of applying and measuring for a range of first input signal frequencies to determine a first resonant frequency and associated bandwidth for acoustic shear wave propagation within the transducer;

positioning the transducer in the temperature and pressure environment of the fluid and in surface contact with the fluid;

applying a second input signal to the transducer to generate acoustic shear waves within the transducer;

measuring the frequency and amplitude of the output signal produced by the transducer in response to the acoustic shear waves;

repeating the steps of applying and measuring for a range of second input signal frequencies to determine a second resonant frequency and associated bandwidth for acoustic shear wave propagation within the transducer; and using the shift between the first and second resonant frequencies and the difference between the first and second bandwidths to calculate the dynamic viscosity of the fluid.

2. The method of claim 1, wherein the step of calculating the viscosity of the fluid further comprises:

calculating the order m of the first and second resonant frequencies from the expression $$m = \frac{a\, \omega_{0m}}{2\pi v}$$

where a is twice the thickness of the transducer, $\omega_{om}$ is the first resonant frequency, and v is the velocity of acoustic shear wave propagation within the transducer;

calculating the phase $\delta$ of the reflection coefficient from the expression $$\delta = -\pi - m2\pi \Delta \omega_m / \omega_{om}$$

where $\Delta\omega_m$ is the shift in the mth resonance;

calculating the amplitude $r_o$ of the reflection coefficient from the expression $$r_o = \exp(\alpha a)\, \frac{1 + \sin((\omega_{1m}/\omega_{0m})m2\pi - \delta - \pi)}{\cos((\omega_{1m}/\omega_{0m})m2\pi - \delta - \pi)}$$

where $\alpha$ is the attenuation in the transducer and $\omega_{1m}$ is the frequency at which the transducer particle displacement in quadrature with the input signal is at a maximum; and calculating the dynamic viscosity $\eta$ by substituting the calculated values for $r_o$ and $\delta$ into the expression $$\eta = \frac{Z_1^2}{\rho \omega}\, \frac{(1 - r_0^2)4r_0 \sin\delta}{[(1 - r_0 \cos\delta)^2 + (r_0 \sin\delta)^2]^2}$$

where $Z_1$ is the acoustical impedance of the viscous medium and $\omega$ is the second resonant frequency.

3. The method of claim 1, wherein the transducer further comprises a piezoelectric transducer; wherein the step of applying a first input signal to the transducer further comprises:

applying a first alternating current input electrical signal to the transducer to generate acustic shear waves within the transducer;

wherein the step of applying a second input signal to the transducer further comprises:

applying a second alternating current input electrical signal to the transducer to generate acoustic shear waves within the transducer; and wherein the steps of measuring the frequency and amplitude of the output signal from the transducer further comprise:

measuring the frequency and amplitude of the output electrical signal produced by the transducer in response to the acoustic shear waves.

4. A method of measuring the dynamic viscosity of a viscous fluid, comprising the steps of:

positioning a first piezoelectric transducer in the temperature and pressure evironment of the fluid and spaced from the fluid;

positioning a second piezoelectric transducer substantially identical to the first transducer in the temperature and pressure environment of the fluid and in surface contact with the fluid;

applying a first input signal to the first transducer to generate acoustic shear waves within the first transducer;

measuring the frequency and amplitude of the output signal produced by the first transducer in response to the acoustic shear waves;

repeating the steps of applying and measuring for a range of first input signal frequencies to determine a first resonant frequency and associated bandwidth fir acoustic shear wave propagation within the first transducer;

applying a second input signal to the second transducer to generate acoustic shear waves within the second transducer;

measuring the frequency and amplitude of the output signal produced by the second transducer in response to the acoustic shear waves;

repeating the steps of applying and measuring for a range of second input signal frequencies to determine a second resinant frequency and associated bandwidth for acoustic shear wave propagation within the second transducer; and using the shift between the first and second resonant frequencies and the difference between the first and second bandwidths to calculate the dynamic viscosity of the fluid.

5. The method of claim 4, wherein the step of calcula5ting the viscosity of the fluid further comprises:

calculating the order m of the first and second resonant frequencies from the expression $$m = \frac{a\, \omega_{0m}}{2\pi v}$$

where a is twice the thickness of the transducer, $\omega_{om}$ is the first resonant frequency, and v is the velocity of acoustic shear wave propagation within the transducer;

calculating the phase $\delta$ of the reflection coefficient from the expression $$\delta = -\pi - m 2\pi \Delta \omega_m / \omega_{om}$$

where $\Delta\omega_m$ is the shift in the mth resinance;

calculating the amplitude $r_o$ of the reflection coefficient from the expression $$r_o = \exp(\alpha a) \frac{1 + \sin((\omega_{1m}/\omega_{0m})m 2\pi - \delta - \pi)}{\cos((\omega_{1m}/\omega_{0m})m 2\pi - \delta - \pi)}$$

where $\alpha$ is the attenuation in the transducer and $\omega_{1m}$ is the frequency at which the transducer particle displacement in quadrature with the input signal is at a maximum; and calculating the dynamic viscosity $\eta$ by substituting the calculated values for $r_o$ and $\delta$ into the expression $$\eta = \frac{Z_1^2}{\rho \omega} \frac{(1 - r_0^2) 4 r_0 \sin\delta}{[(1 - r_0 \cos\delta)^2 + (r_0 \sin\delta)^2]^2}$$

where $Z_1$ is the acoustical impedance of the viscous medium and $\omega$ is the second resonant frequency.

* * * * *

UNITED STATES PATENT AND TRADEMARK OFFICE
CERTIFICATE OF CORRECTION

PATENT NO. : 4,862,384
DATED : August 29, 1989
INVENTOR(S) : Martial R. Bujard and Bernhard R. Tittmann It is certified that error appears in the above-identified patent and that said Letters Patent is hereby corrected as shown below:

On the first page, the named inventors should include

----Bernhard R. Tittmann, Thousand Oaks, California----.

Signed and Sealed this

Third Day of April, 1990

Attest:

HARRY F. MANBECK, JR.

*Attesting Officer*  *Commissioner of Patents and Trademarks*